United States Patent [19]

Schwab

[11] Patent Number: 4,911,640
[45] Date of Patent: Mar. 27, 1990

[54] MAGNETIC ASSEMBLY MEANS

[75] Inventor: Michel Schwab, Bienne, Switzerland

[73] Assignee: Comadur SA, La Chaux-de Fonds, Switzerland

[21] Appl. No.: 187,692

[22] Filed: Apr. 29, 1988

[30] Foreign Application Priority Data

Apr. 30, 1987 [FR] France ................ 87 06228

[51] Int. Cl.[4] .......................... A61C 13/235
[52] U.S. Cl. .................... 433/189; 335/302; 403/DIG. 1
[58] Field of Search ............ 433/189; 335/302, 303; 403/DIG. 1

[56] References Cited

U.S. PATENT DOCUMENTS

| 2,698,917 | 1/1955 | Van Urk et al. | 335/302 |
| 2,975,497 | 3/1961 | Budreck | 335/302 |
| 4,431,419 | 2/1984 | Portnoy | 433/189 |

FOREIGN PATENT DOCUMENTS

| 3140464 | 4/1983 | Fed. Rep. of Germany | 433/189 |
| 2586926 | 3/1987 | France | 433/172 |
| 2587895 | 4/1987 | France | 433/189 |
| 2598314 | 11/1987 | France | 433/189 |

Primary Examiner—John J. Wilson
Attorney, Agent, or Firm—Sughrue, Mion, Zinn, Macpeak & Seas

[57] ABSTRACT

An assembly having a capsule containing a permanent magnet housed in a casing which is closed by a cover. The cover and the casing are both of ferromagnetic material. The bottom of the casing and the wall thereof are connected to each other by a narrow peripheral partition forming a saturable zone having high magnetic reluctance. The lines of flux developed by the magnet are thus concentrated through the base of the wall of the casing. The assembly is useful inter alia for the retention of dental prostheses.

14 Claims, 2 Drawing Sheets

MAGNETIC ASSEMBLY MEANS

FIELD OF THE INVENTION

The present invention relates to magnetic assembly means having a permanent magnet as a source of magnetic potential generating assembly forces. More specifically, the invention relates to assembly means of this type suitable for use in chemically aggressive environments without there being any possible detrimental influence on the assembly forces.

Such assembly means may, for example, be used in odontology for maintaining dental prostheses in place.

DESCRIPTION OF THE PRIOR ART

U.S. Pat. No. 4,431,419 discloses retaining means for dental prostheses having a cap rigid with the dental prosthesis and having a housing of a ferromagnetic material with a permanent magnet housed therein. This housing forms part of a magnetic circuit which is closed, when the prosthesis is in place, by a ferromagnetic counterpiece anchored in the denture. The housing is hermetically sealed by a covering layer which protects the magnet from the salivary environment.

In this earlier device the covering layer is of a plastics material, more specifically acrylic resin which covers one of the faces of the magnet and which is sealed to the inner periphery of the wall of the casing.

When the cap and the counterpiece are assembled, this covering layer is interposed between the magnet and the counterpiece, thereby providing a flux gap, i.e. a high reluctance passage in relation to the circulation of flux developed by the permanent magnet. An assembly force is thus achieved which is much smaller than the force which the magnet could develop in the absence of the flux gap.

Another disadvantage of this earlier arrangement resides in the fact that a considerable part of the magnetic flux circulates along the leakage path through areas of the mouth in the vicinity of the prosthesis which could be harmful to the wearer thereof, causing dentists to be reluctant to use such prostheses for their patients French patent application No. 86.06805 dated May 9, 1986 provides an initial solution to the problems associated with the assembly means of U.S. Pat. No. 4,431,419 in that it proposes the replacement of the covering layer of plastics material by a covering layer formed from a very thin pellet made of a permanent magnetic material.

However, whilst this solution does provide an improvement in respect of the magnetic aspect, since it succeeds in reducing the size of the flux gap, on the other hand, it creates manufacturing and sealing problems since the pellet has to be welded to the casing or mounted between the edge of the peripheral wall of the casing and the magnet itself. Moreover, it is difficult to produce a thin pellet of this type.

BRIEF DESCRIPTION OF THE INVENTION

It is an object of the invention to provide permanent magnetic assembly means combining good protection for the magnet with maximum efficiency of magnetic attraction, rendering it particularly suitable for use in odontology.

It is thus an object of the invention to provide magnetic assembly means for the assembly of two objects, the first of which has a magnetized capsule and the second a counterpiece of a ferromagnetic material, said capsule comprising, on the one hand, a casing of a ferromagnetic material in which a permanent magnet is housed and which forms part of a magnetic circuit for the flux of the magnet, the circuit being closed by said counterpiece when the two objects are assembled and, on the other hand, a cover for hermetically sealing said casing, wherein said cover is of a ferromagnetic material and the bottom and the wall of the casing are connected to one another by a thin peripheral partition constituting a saturable zone and defining a boundary at the base of said wall of a peripheral polar piece which forms, with said counterpiece and said bottom, a path of weak reluctance for the flux of said magnet.

As a result of these features, the magnetic circuit conveying the flux of the permanent magnet is closed through the bottom of the casing, the counterpiece and the lateral wall of the casing, without interposition of a flux gap, because the bottom and the peripheral base of this lateral wall can rest directly on the counterpiece. The lines of magnetic force developed by the permanent magnet are thus virtually entirely utilized.

Complete tightness is guaranteed at the interface of the capsule and the counterpiece since the bottom, the intermediate partition and the lateral wall are formed in one piece. It is then relatively simple to provide a tight closure on the cover side by means of welding for example, the cover and the casing both being made of ferromagnetic material. Moreover, the part of the casing opposite the counterpiece can easily be lodged in the object which receives the capsule to ensure even better tightness. This is notably the case in the application of the means for the retention of dental prostheses in which the capsule can be moulded within the structure of the prosthesis with only the outer face on the counterpiece side of the capsule being exposed.

BRIEF DESCRIPTION OF THE DRAWINGS

The invention will be better understood from a study of the following description give as an example of the embodiment of the invention.

In the attached drawings, given solely for purposes of illustration.

DETAILED DESCRIPTION OF EMBODIMENTS OF THE INVENTION

Whilst the following description is specifically related to the application of the invention to odontology it is clear that the magnetic assembly means of the invention can be advantageously employed in all instances where it is necessary to provide good bonding between two objects with minimal space occupied by the assembling means and providing effective protection for the magnet in the environmental medium.

Figure 1:
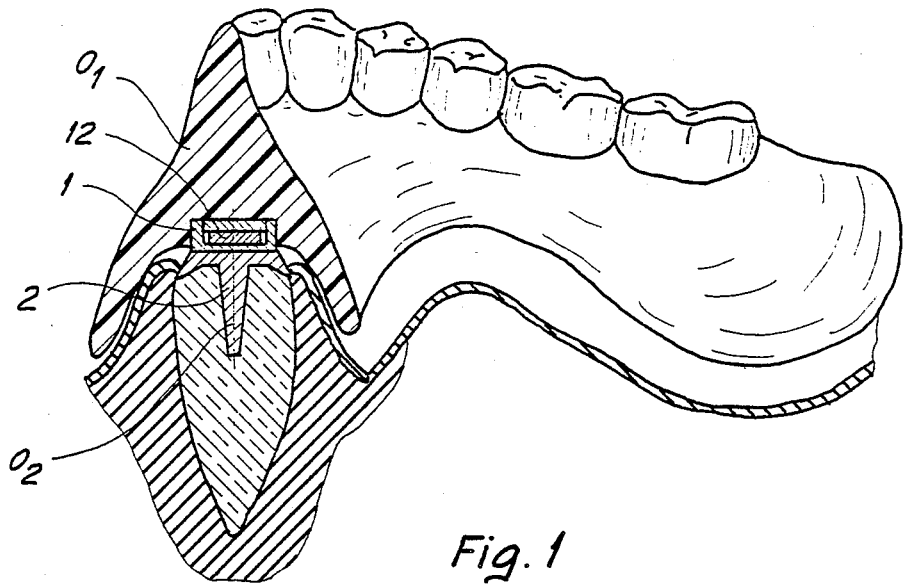
FIG. 1 shows an overall sectional view of a magnetic assembly means according to the invention as used for retaining a dental prosthesis.

FIG. 1 shows a magnetic assembly means the capsule 1 of which is fixed in the first object $O_1$, namely a dental prosthesis, the counterpiece 2 of which is anchored in the second object $O_2$, in this case the root of a tooth.

Figure 2:
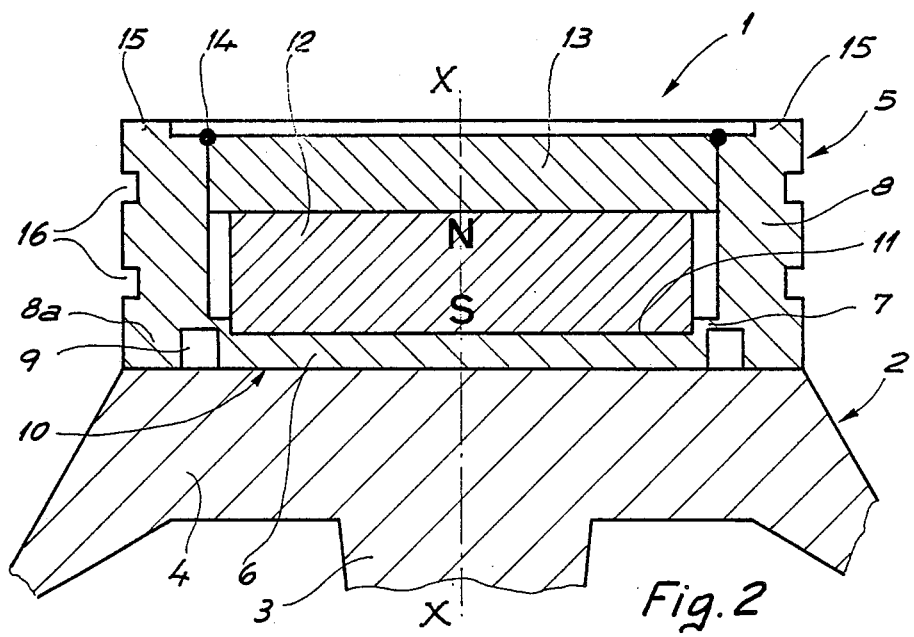
FIG. 2 is a sectional view on a larger scale of the assembly means of the invention.

The counterpiece or implant 2 is formed by a shank 3 (FIG. 2) designed to be cemented in conventional manner into the radicular channel of the root of the tooth, this shank being surmounted by a cover 4 adapted to the shape of the gingival mucosa. This cover may be circular.

The capsule 1 comprises a casing 5 made of ferromagnetic material such as an alloy of the ferro-nickel type having high saturation induction. The material sold under the Trade Mark "Permanom" by Vacuum Schmelz of Hanau, Federal Republic of Germany is suitable. The outer shape of the casing 5 can be other than cylindrical, particularly in the case of an application differing from that envisaged herein.

The casing 5 has a bottom 6, a peripheral partition 7 enclosing this bottom and an outer wall 8, the base 8a of which is partially indented by a circular groove 9 opening towards the operational surface 10 of the capsule (the lower surface of the capsule in the position shown in the figures). The depth of this groove determines the thickness of the partition 7 and to a considerable extent the magnetic behaviour of the assembly.

The bottom 6 is hollowed out to form a housing 11 for the lower part of the permanent magnet 12, the north and south poles of which are situated on the two opposing surfaces, it being understood that the magnet can be placed in an opposite position to that shown. The flux developed by this magnet is thus oriented along the X—X axis of the assembly means. The magnet 12 is preferably made of an alloy having a high energy product, such as for example samarium-cobalt.

A cover 13 of ferromagnetic material is fitted in the top of the casing 5. It is fixed in place with the aid of a peripheral welding band 14 obtained, for example, by laser welding. To prevent this band from projecting beyond the upper face of the capsule 1, the outer wall 8 is provided with a raised annular edge 15.

The outer cylindrical surface of the wall 8 is provided with two annular grooves 16 to permit the capsule 1 to be anchored in the body of the dental prosthesis.

Figure 3:
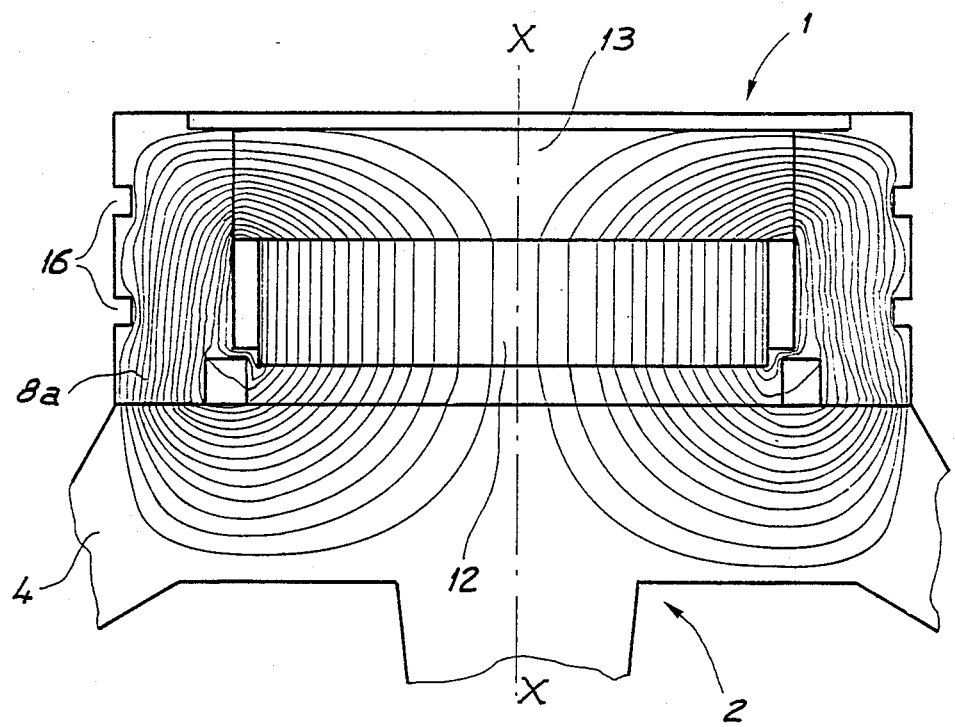
FIG. 3 is a diagram of the lines of flux developed by the magnet in the magnetic assembly means.

FIG. 3 shows a diagram of the lines of force of the magnetic field generated in the capsule 1. The narrow passage formed by the peripheral partition 7 is so dimensioned that it is saturated in order to constitute a zone of very high magnetic reluctance. The lines of force are thus concentrated through the base 8a of the peripheral wall of the casing where they create a high attractive force. This base thus forms a peripheral polar piece.

These lines of force pass into the cover 4 and return to the bottom 6 without passing through a flux gap capable of creating any substantial magnetic reluctance. To reduce this reluctance at the flux gap to a negligible value the contact faces are preferably carefully polished.

From the opposite side of the magnet the lines of force circulate through the cover 13 and from there into the outer wall 8 also without encountering a flux gap, the cover 13 being adapted with precision to the diameter of the opening of the casing 5.

It has been found in practice that a casing of an outer diameter of the order of 4.5 mm, of a height of 2.00 mm, provided with a samarium-cobalt magnet of a diameter in the region of 3 mm and a height of about 1 mm can have a partition 13 the thickness of which is between 0.05 and 0.1 mm depending on the forces of attraction to be achieved. It is clear that different dimensions of the assembly means are possible both in the framework of the foregoing application and in other applications of the invention.

Reverting to FIG. 1 it is apparent that, as compared with the prior art proposals, the assembly means for dental prostheses of the invention has a capsule 1 which is positioned in inverted condition, i.e. with a bottom which is applied to the cover of the implant. On its opposite face this capsule is in direct contact with the plastics materials of which the dental prosthesis is composed. There results perfect tightness of the capsule and effective protection for the magnet against attack by the salivary medium. The magnet thus retains all its magnetic properties regardless of the duration of use of the prosthesis.

It has also been found that the magnetic flux is contained virtually integrally inside the pieces of the assembly means with the result that it is biocompatible without having an unfavourable effect on the biological environment due to escaping magnetic flux.

It is moreover clear for odontological specialists that the counterpiece can be fixed in the mouth in a manner differing from that shown, for example, laterally on the crown of a tooth of a prosthesis, the counterpiece then being adapted accordingly.

Figure 4:
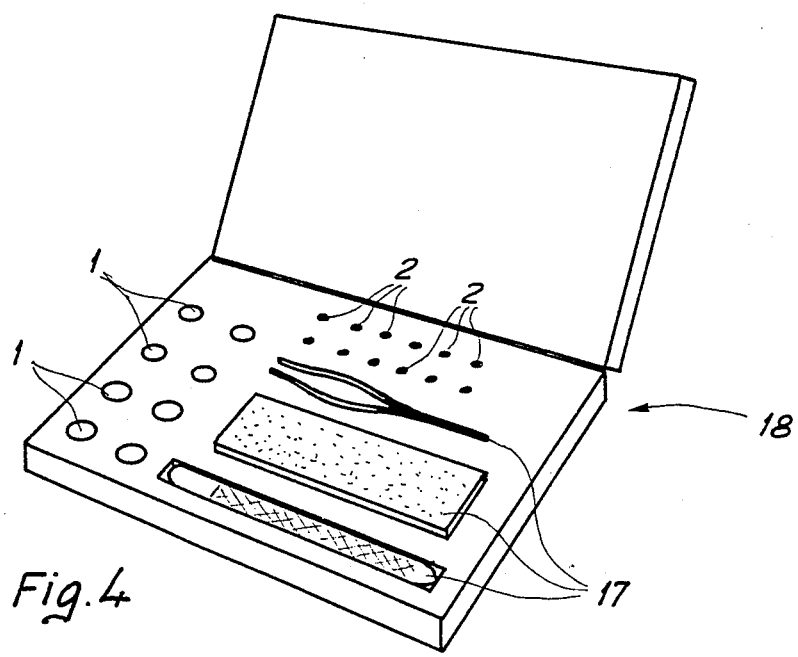
FIG. 4 is a general view of a dental kit also according to the invention.

FIG. 4 shows that the invention can be executed in the form of a kit 17 for the preparation of dental prostheses comprising, apart from several instruments 18 known per se, a set of assembly means according to the invention each composed of a capsule 1 and a counterpiece or implant 2 and enabling the practitioner to choose from amongst the different pieces of different sizes those best suited for his patient.

What is claimed is:

1. Magnetic assembly means for the assembly of a first and a second object wherein said first object is a magnetic capsule and said second object is a ferromagnetic counterpiece, said magnetic capsule having a permanent magnet, a ferromagnetic casing and a ferromagnetic cover, said permanent magnet being housed within said ferromagnetic casing and being hermetically sealed from potentially hostile environments by said cover, said ferromagnetic casing having a bottom portion, a wall portion and a thin peripheral partition,
   said thin peripheral partition interconnecting said bottom portion to said wall portion,
   said thin peripheral partition constituting a magnetically saturable zone and defining a boundary, at the base of said wall portion, of a peripheral polar portion,
   whereby said peripheral polar portion, said counterpiece and said bottom portion taken together form a low reluctance magnetic flux path for the flux of said permanent magnet.

2. Magnetic assembly means according to claim 1, wherein, in assembled configuration, the cover of the casing is situated in the face of the latter opposite the face which is to be adjacent to said counterpiece.

3. Magnetic assembly means according to claim 1, wherein said capsule is of cylindrical shape with a circular base.

4. Magnetic assembly means according to claim 1, wherein said peripheral partition is situated between the bottom of the casing and the base of its peripheral wall and is bound by an annular groove sunk into the face of the capsule which is to be adjacent to the counterpiece of the means in the assembled configuration.

5. Magnetic assembly means according to claim 1, wherein said magnet is disposed at least partially in a housing provided in the inside of the bottom of the casing.

6. Magnetic assembly means according to claim 1, wherein said cover is formed by a washer fitted in the opening of said casing and fixed thereto by means of a peripheral weld.

7. Magnetic assembly means according to claim 1 wherein said thin peripheral partition is thinner than either said bottom portion or said wall portion, and has a higher reluctance magnetic flux path for the flux of said permanent magnet, thereby concentrating the magnetic flux through, and creating a high magnetic attractive force at said base of said wall portion.

8. A magnetic assembly means according to claim 7 in which said counterpiece is shaped as a dental implant for the radicular channel of the root of a tooth, and said capsule is adapted to be fixed in a dental prosthesis.

9. A kit for the manufacture of a dental prosthesis comprising at least one magnetic assembly means comprising a magnetic capsule, adapted to be incorporated into said prosthesis, and one ferromagnetic counterpiece adapted to be fixed on the tooth of a patient;
said magnetic capsule having a permanent magnet, ferromagnetic casing and a ferromagnetic cover, said permanent magnet being housed within said ferromagnetic casing and being hermetically sealed from potentially hostile environments by said cover, said ferromagnetic casing having a bottom portion, a wall portion and a thin peripheral partition,
said thin peripheral partition interconnecting said bottom portion to said wall portion,
said thin peripheral partition constituting a magnetically saturable zone and defining a boundary, at the base of said wall portion, of a peripheral polar portion,
whereby said peripheral polar portion, said counterpiece and said bottom portion taken together form a low reluctance magnetic flux path for the flux of said permanent magnet.

10. A kit according to claim 9 wherein said thin peripheral partition of said magnetic assembly means is thinner than either said portion or said wall portion, and has a higher reluctance magnetic flux path for the flux of said permanent magnet, thereby concentrating the magnetic flux through, and creating a high magnetic attractive force at said base of said wall portion.

11. A dental prosthesis comprising a magnetic capsule fixed in said prosthesis and forming part of a magnetic assembly means which also includes a ferromagnetic counterpiece adapted to be anchored in the root of a patient's tooth;
said magnetic capsule having a permanent magnet, ferromagnetic casing and a ferromagnetic cover, said permanent magnet being housed within said ferromagnetic casing and being hermetically sealed from potentially hostile environments by said cover, said ferromagnetic casing having a bottom portion, a wall portion and a thin peripheral partition,
said thin peripheral partition interconnecting said bottom portion to said wall portion,
said thin peripheral partition constituting a magnetically saturable zone and defining a boundary, at the base of said wall portion, of a peripheral polar portion,
whereby said peripheral polar portion, said counterpiece and said bottom portion taken together form a low reluctance magnetic flux path for the flux of said permanent magnet.

12. A dental prosthesis according to claim 11 wherein said thin peripheral partition of said magnetic assembly means is thinner than either said bottom portion or said wall portion, and has a higher reluctance magnetic flux path for the flux of said permanent magnet, thereby concentrating the magnetic flux through, and creating a high magnetic attractive force at, said base of said wall portion.

13. Magnetic assembly means for the assembly of two objects the first of which has a magnetic capsule and the second a counterpiece of a ferromagnetic material, said capsule comprising on the one hand a casing of a ferromagnetic material in which is housed a permanent magnet and which forms part of a magnetic circuit for the flux of the magnet, the circuit being closed by said counterpiece when the two objects are assembled and, on the other hand, a cover for the hermetic sealing of said casing wherein said cover is of a ferromagnetic material, in that the bottom and the wall of the casing are connected to one another by a thin peripheral partition constituting a saturable zone delimiting at the base of said wall a peripheral polar piece which, with said counterpiece and said bottom, forms a path of low reluctance for the flux of said magnet.

14. Magnetic assembly means according to claim 13 wherein said thin peripheral partition is thinner than either said bottom or said wall, and has a higher reluctance magnetic flux path for the flux of said permanent magnet, thereby concentrating the magnetic flux through, and creating a high magnetic attractive force at, said base of said wall.

* * * * *